US009010269B2

(12) United States Patent
Bala et al.

(10) Patent No.: US 9,010,269 B2
(45) Date of Patent: Apr. 21, 2015

(54) STERILIZATION CHALLENGE SPECIMEN HOLDER COUNTER

(75) Inventors: Harry Bala, South Barrington, IL (US); Mark Bala, Chicago, IL (US)

(73) Assignee: Dana Products, Inc., Franklin Park, IL (US)

( * ) Notice: Subject to any disclaimer, the term of this patent is extended or adjusted under 35 U.S.C. 154(b) by 305 days.

(21) Appl. No.: 13/537,512

(22) Filed: Jun. 29, 2012

(65) Prior Publication Data
US 2014/0000506 A1    Jan. 2, 2014

(51) Int. Cl.
| A61L 2/26 | (2006.01) |
| G06M 1/24 | (2006.01) |
| G01D 9/02 | (2006.01) |
| A61L 2/28 | (2006.01) |

(52) U.S. Cl.
CPC .... *G01D 9/02* (2013.01); *A61L 2/28* (2013.01)

(58) Field of Classification Search
CPC ............. A61L 2/26; A61L 2/28; G06M 1/04; G06M 1/041; G06M 1/045; G06M 1/08; G06M 1/083; G06M 1/22; G06M 1/24
USPC ......... 116/281, 282, 283, 284, 285, 299, 306, 116/307, 314, 315, 319, 320, 321, 323, 116/324; 222/36, 37, 38, 41, 46, 49; 235/117 A, 117 R, 118, 124; 422/560, 422/565
See application file for complete search history.

(56) References Cited

U.S. PATENT DOCUMENTS

| 443,969 | A | * | 12/1890 | Massey | ........................... 101/77 |
| 2,032,304 | A | * | 2/1936 | Padgett | ......................... 116/282 |
| 2,417,114 | A | * | 3/1947 | Kilham | ......................... 116/282 |
| 2,759,666 | A | * | 8/1956 | Wyckoff | ....................... 235/1 B |
| 3,092,317 | A | * | 6/1963 | Viele | ......................... 235/91 PR |
| 3,112,066 | A | * | 11/1963 | Brame | ........................... 235/118 |
| 3,118,232 | A | * | 1/1964 | Hartsock | ......................... 33/810 |
| 3,229,659 | A | * | 1/1966 | Sciascia | ......................... 116/282 |
| 4,342,391 | A | * | 8/1982 | Schainholz | ................... 206/370 |
| 5,359,993 | A | * | 11/1994 | Slater et al. | .................... 600/133 |
| 6,779,715 | B2 | * | 8/2004 | Williams | .................. 235/144 D |

FOREIGN PATENT DOCUMENTS

| EP | 581400 A1 | * | 2/1994 | ............. G06M 1/08 |
| GB | 2407187 A | * | 4/2005 | ............. G06M 1/08 |

* cited by examiner

*Primary Examiner* — R. A. Smith
(74) *Attorney, Agent, or Firm* — Levenfeld Pearlstein, LLC

(57) ABSTRACT

A counting device includes a shaft, a handle affixed to a first end of the shaft, and a locking unit mounted in the handle spaced from the shaft. A locking plate has an opening for accommodating the shaft. The locking plate has a plurality of recesses facing the locking unit for cooperating with the locking unit. A position indicating assembly is coupled to the shaft to move as the handle is rotated. The recesses are arranged in a circular pattern on the locking plate such that the locking unit engages each recess as the handle is rotated around the shaft. The recesses are configured to permit one-way rotation of the handle.

17 Claims, 3 Drawing Sheets

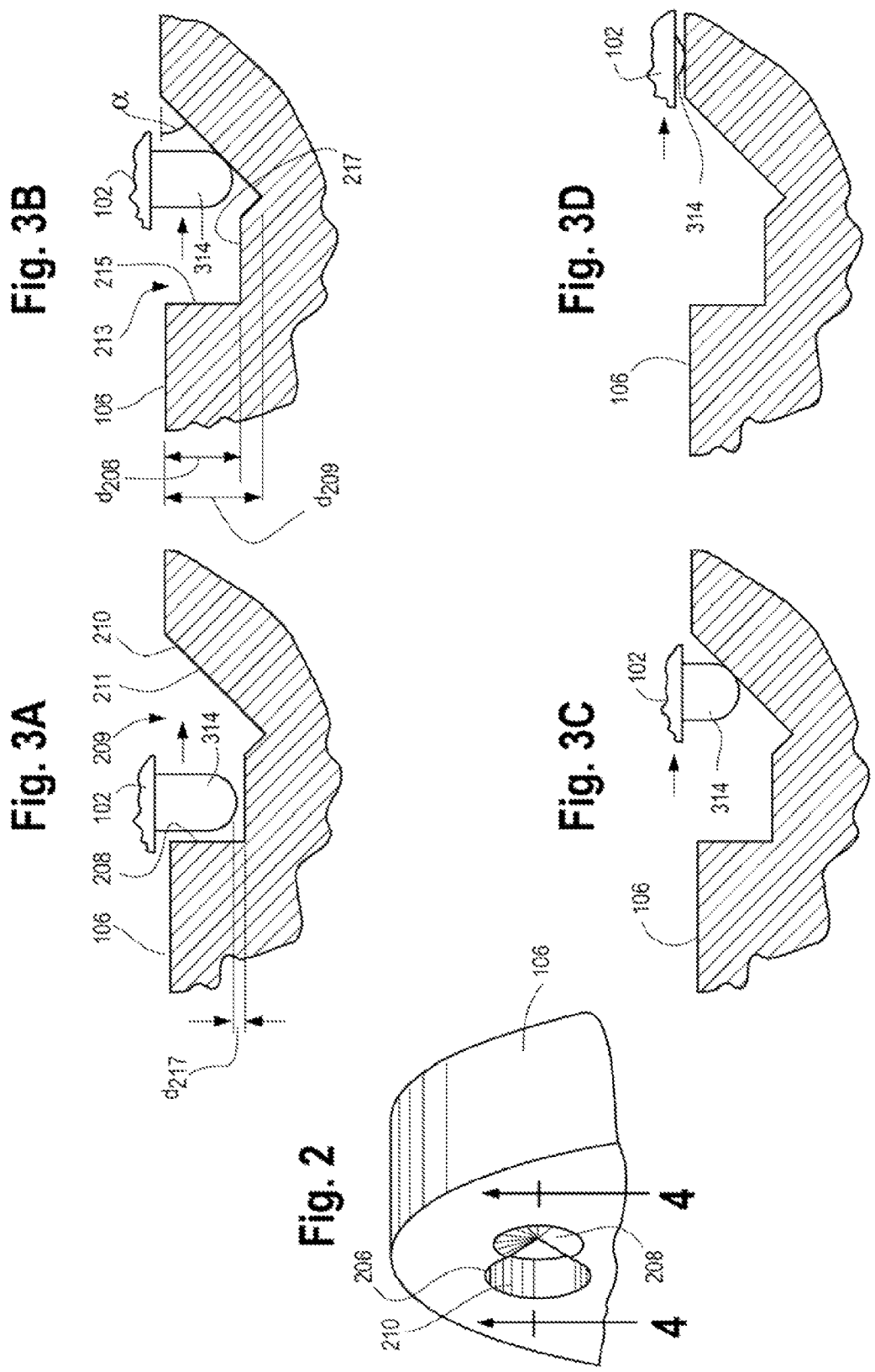

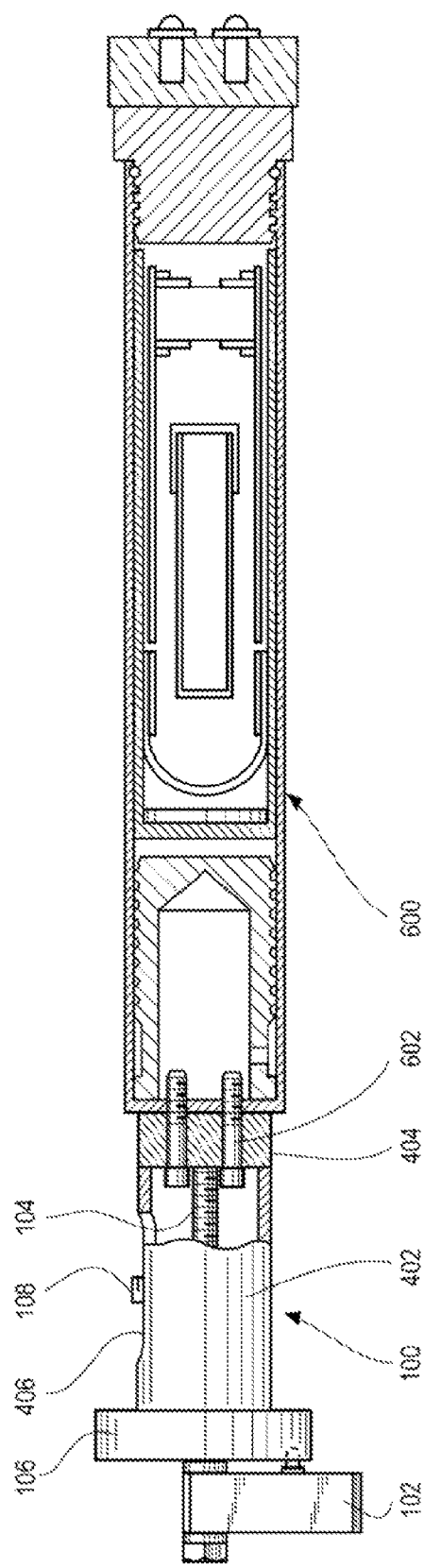

STERILIZATION CHALLENGE SPECIMEN HOLDER COUNTER

BACKGROUND

Many devices have a predetermined useful life based upon the number of times the device operates. These types of devices are typically discarded or refurbished after the predetermined number of uses occurs. The continued use of devices beyond the predetermined number of uses may lead to deteriorated performance, failure of the device, or may generate undesirable results.

One example of a device that is retired or refurbished after a predetermined number of uses is a sterilization challenge specimen holder. A sterilization challenge specimen holder is used to hold a biological indicator during a sterilization cycle to provide a consistent challenge to sterilization. Examples of such holders are disclosed in Bala, U.S. Pat. Nos. 7,718,125; 7,740,802; 7,790,105; and 7,811,516, all of which are commonly assigned with the present application and are incorporated herein by reference. Due to concerns regarding thermal effects of cycling, after a specific number of uses, the performance of the sterilization specimen holder is assumed to be compromised. Accordingly, the holder must be refurbished or discarded after the predetermined number of uses has occurred.

It is, however, difficult to track the number of times the holder is used to sterilize materials because the holder does not include a mechanism to count the number of uses. Further, requiring documentation of uses on an instrument separate from the holder can lead to errors in counting due to operators forgetting to record uses of the device. Based on these concerns, a need exists for a device that can be mounted directly to a holder that facilitates counting the number of times the holder has been used.

SUMMARY

Various embodiments of the present disclosure include a mechanical counting device that includes a shaft, a handle affixed to a first end of the shaft and a locking unit on the handle spaced from the shaft. A locking plate has a central opening to accommodate the shaft and is spaced from the handle.

The locking plate has a plurality of recesses therein facing the locking unit engagement unit. A position indicating assembly is rotatably coupled to the shaft, which moves longitudinally along the shaft as the handle is rotated. The recesses are arranged in a circular pattern on the locking plate such that the locking unit engages each recess as the handle is rotated around the shaft. The recesses are configured to permit one-way rotation of the handle.

Other embodiments of the present disclosure include a method of counting the uses of a device via a counting device, and includes the steps of rotating a handle affixed to a first end of a shaft, the handle including a locking unit on the handle spaced from the shaft. A locking plate has an opening to accommodate the shaft and includes a plurality of recesses having entrance and exit portions. A position indicating assembly is rotatably coupled to the shaft and moves longitudinally along the shaft as the handle is rotated. The recesses are arranged in a circular pattern on the locking plate such that the locking unit engages each recess as the handle is rotated around the shaft. The recesses permitting only one-way rotation of the handle.

Other objects, features, and advantages of the disclosure will be apparent from the following description, taken in conjunction with the accompanying sheets of drawings, wherein like numerals refer to like parts, elements, components, steps, and processes.

BRIEF DESCRIPTION OF THE DRAWINGS

FIG. 2 is a perspective view of a locking plate recess;

FIGS. 3A-3D illustrates a locking unit finger in and moving through a recess in the locking plate; and FIG. 4 illustrates a the counter of FIG. 1 mounted to an exemplary sterilization challenge specimen holder.

DETAILED DESCRIPTION

Figure 1:
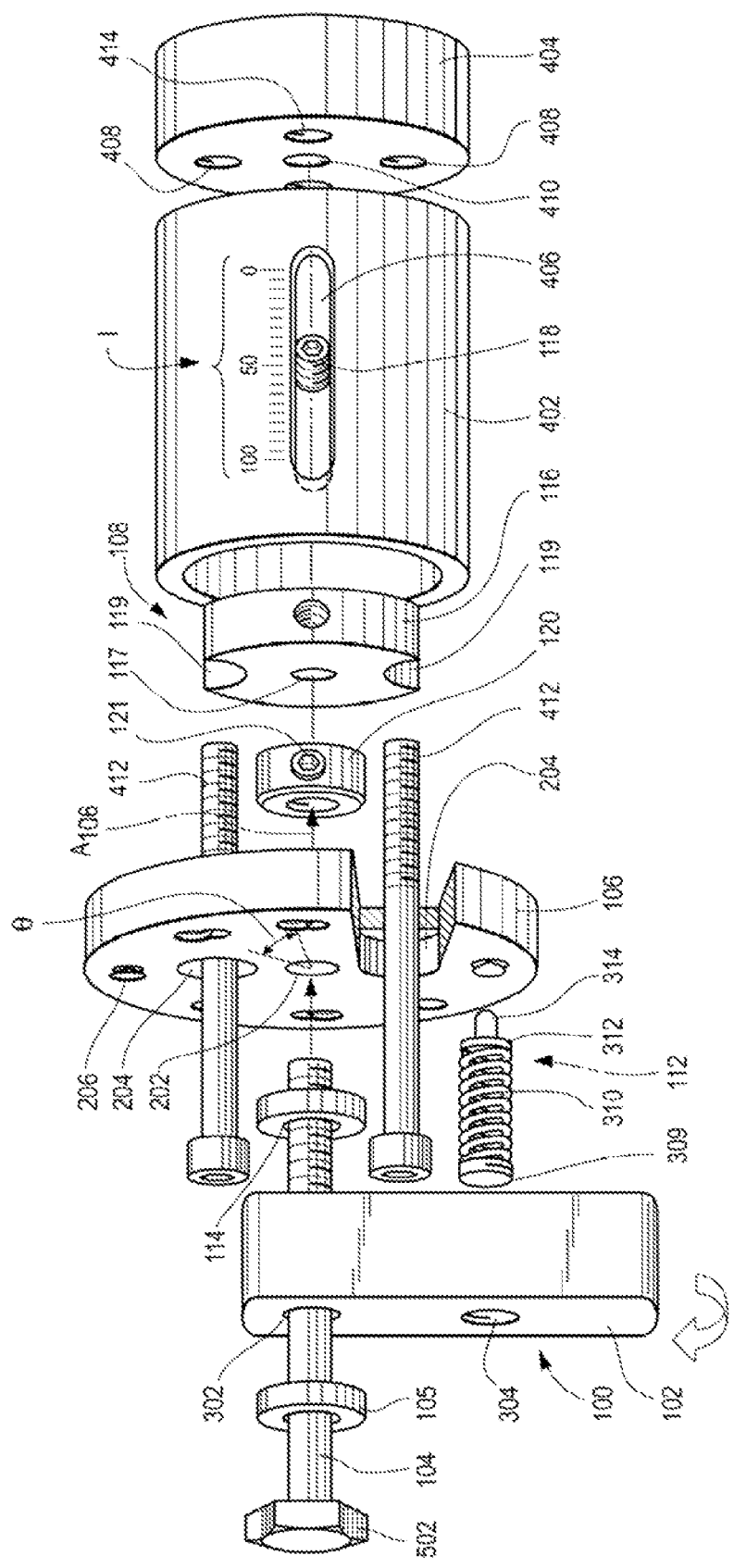
FIG. 1 is an exploded view of a counter for a sterilization challenge specimen holder.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 is an exploded view of a sterilization challenge specimen holder counter 100. The counter 100 includes a handle 102 having an opening 302 that is sized to accommodate a threaded shaft or post 104, a locking plate 106, and a position indicator assembly 108. The shaft 104 may be a bolt, a screw, a threaded rod, or any other device capable of connecting the handle 102 to the position indicator assembly 108. The shaft 104 and handle 102 are fixed mounted to one another so that rotation of the handle 102 results in rotation of the shaft 104. In a present embodiment, the shaft 104 is formed as a bolt, and a lock washer 105 is positioned between the head 502 of the bolt and the handle 102.

The shaft 104 passes through an opening 202 in the center of the locking plate 106. The locking plate 106 includes a plurality of locking recesses 206, described in more detail below, formed in the locking plate 106 facing the handle 102. The recesses 206 are sized to cooperate with a biased locking unit 112 on the handle 102 to permit the handle 102 to be rotated in one direction (a forward direction), but to prevent rotation in the opposite direction (a rearward or backward direction). The handle 102 is separated from the locking plate 106 by a spacing unit 114 having an opening sized to accommodate the shaft 104.

The position indicator assembly 108 includes a central plate 116 having a threaded opening 117 that is sized to threadedly mate with the shaft 104, and an indicator 118 that extends from an edge of the plate 116. A locking ring 120 is positioned on the shaft 104 adjacent to the plate 106, between the plate 106 and the position indicator assembly 108. The locking ring 120 is secured to the shaft 104, by, for example, set screws 121, to prevent the locking plate 106 and shaft 104 from longitudinally moving relative to one another (as when the handle 102/shaft 104 are rotated).

It will be appreciated that absent the locking unit 112, as the handle 102 and shaft 104 are rotated, the plate 116 which is threadedly engaged with the shaft 104, will move along the shaft 104. As such, the location of the plate 106 along the shaft 104 will correlate to the number of turns of the shaft 104.

The locking plate 106, in conjunction with the locking unit 112 and handle 102, permit only one-way rotation of the shaft 104. The plate 106 is substantially circular, and includes a central opening 202 through which the shaft 104 passes, at least two securing openings 204, and the recesses 206. The recesses 206 are arranged along a circular path on the locking plate 106 a distance so as to cooperate with the locking unit 112.

The locking unit 112 includes a cap 309, a spring 310, a collar 312, and an engaging finger 314. The finger 314 is positioned in the collar 312 such that a lower portion of the finger 314 is secured by and extends beyond an end of the collar 312 (see, e.g., FIG. 3A). The upper portion of the finger 314 is coupled to a spring 310 which biases the finger 314 out of the handle 102. The locking unit 112 is positioned in opening 304 in the handle 102. A force applied on the finger 314 against the bias or spring 310 urges the finger 314 into the handle 102.

FIG. 2 is a perspective view of one of the recesses 206 in the locking plate 106. As set forth above, the locking unit 112, in conjunction with the locking plate 106 and recesses 206 allow one-way rotation of the handle 102 relative to the plate 106. Accordingly, each recess 206 includes an entrance portion 208 and an exit portion 210 contiguous with one another. The exit portion 210 of the recess 206 is formed with a machined conical or countersunk region 209 with an upwardly angled exit wall 211. In a present recess 206, the exit portion wall 211 is formed at an angle α of about 45 degrees to the surface of the plate 106. The entrance portion 208 is formed as a machined or carved out section 213 with a straight entrance side wall 215. The entrance portion 208 is machined out to a depth $d_{208}$ that is less than the depth $d_{209}$ of the countersunk region.

In a present recess 206, the countersunk exit region 209 is formed to a depth $d_{209}$ of about 0.093 inches and the entrance side straight side wall 215 is formed to a depth $d_{208}$ of about 0.065 inches, essentially creating a step 217 in the recess 206. The finger 314 is configured so that it rides on the surface of the plate 106 and drops (by action of the spring 310) into the recess 206 at the entrance region. As the handle 102 is further rotated, the finger 314 moves up along the angled exit region wall 211 (see, e.g., FIGS. 3B and 3C), and is urged back up into the handle 102 as the handle 102 moves beyond the recess 206. However, rearward movement of the handle 102 is prevented by contact of the finger 314 with the straight side wall 215 of the entrance region 208. In a preferred embodiment, the finger 314 projects into the recess 206, but does not contact the bottom of the carved out region (the step 217), and most preferably, is a distance $d_{217}$ of about 0.06 inches from the step 217.

Returning to FIG. 1, the counter 100 includes a cover 402 that covers the lower portion of the counter 100, and a cap 404. The cover 402 includes a slot 406 that is sized to accommodate the indicator 118 on the central plate 116. The counter 100 is held together by fasteners 412, such as the illustrated shoulder bolts that extend through the locking plate 106 and are received in openings 408 in the cap 404. The central plate 116 includes two notches 119 through which the bolts 412 pass as they extend from the locking plate 106 to the end cap 404.

As the handle 102 is rotated around the locking plate 106 in the forward direction, the finger 314 drops (by spring 310 force) into each recess 206. In further urging the handle 102 in the forward direction, because the exit portion 210 has an upwardly sloping wall 211, the finger 314 can move up and out of the recess 206 to advance to the next recess. However, because of the recess straight rear wall 215 (entrance portion 208), engagement of the finger 314 with the wall 215 prevents backward rotation of the handle 102.

When the counter 100 is assembled, the handle 102 is coupled to the locking plate 106 by the shaft 104. The locking ring 120 holds the locking plate 106 against the spacing unit 114 and handle 102. The locking ring 120 is configured to prevent the shaft 104 from separating from the locking plate 106 as the handle 102 is rotated. Because the shaft 104 is secured to the handle 102, and the locking plate 106 is coupled to the handle 102, the shaft 104 rotates around the central axis $A_{106}$ of the plate 106

As the shaft 104 is rotated, the position indicator assembly 108 moves longitudinally along the length of the shaft 104. The indicator 118 and notches 119 on the central plate 116 prevent the plate 116 from rotating with the shaft 104. Accordingly, by rotating the handle 102, the position indicator assembly 108 moves longitudinally along the shaft 104 toward the locking plate 106. And, as set forth above, the handle 102 can only be rotated in one direction due to interference between the finger 314 and the recess entrance wall 215 when it is attempted to rotate the handle 102 in a backward or rearward direction.

The recesses 206 are positioned along the surface of the locking plate 106 such that the movement from one recess 206 to an adjacent recess 206 results in the position indicator 108 moving a predetermined distance within the slot 406. The angle Θ between adjacent recesses 206 (e.g., 360 degree rotation of the handle 102 divided by the number of recesses 206), in conjunction with the pitch of the threads on the shaft 104 (e.g., the number of threads per inch of the shaft 104) corresponds to a predetermined linear distance of movement along the shaft 104.

For example, if the shaft 104 has a thread pitch of 20 threads per inch, then rotation of the shaft 20 times will result in movement of the indicator 118 one inch along the length of the shaft 104. With eight recesses in the plate 106, one hundred sixty (160) discrete movements of the handle 102 will result in 1 inch of movement of the indicator 118. Viewed another way if it is determined that the holder 600 has a useful life of 200 cycles, then movement of the indicator 118 (200/(8×20)) or 1.25 inches will indicate that the holder 600 has reached its useful life. Accordingly, indicia can be provided on the cover 402, adjacent to the slot 406 (as illustrated in FIG. 1), to provide such indication of the number of uses or the percent of useful life remaining or used.

FIG. 4 illustrates the counter 100 coupled to a sterilization challenge specimen holder 600. The counter 100 is coupled to the holder 600 by fasteners, such as bolts 602 that pass through the openings 414 in the end cap 404. After the counter 100 is installed, a user rotates the handle 102 clockwise before or after each use to increment the indicator 118. When the maximum number of uses of has been reached, the holder 600 can be returned to be refurbished or disposed of as desired.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A counting device, comprising:
   a threaded shaft;

a handle affixed to a first end of the threaded shaft, the handle including a locking unit on the handle spaced from the shaft;

a locking plate having an opening therein for receipt of the shaft, the locking plate spaced from the handle, the locking plate having a plurality of recesses in facing relation to the locking unit; and a position indicating assembly unit coupled to the threaded shaft for movement as the handle is rotated, the position indicating assembly unit including a position indicator; and indicia disposed for cooperation with the position indicator, wherein the recesses are arranged in a circular pattern in the locking plate and cooperate with the locking unit such that the locking unit engages each of the recesses as the handle is rotated, and wherein rotation of the handle moves the position indicator to indicate a count of handle movements, and wherein the counting device includes a cover having an opening therein to accommodate the position indicator.

2. The counting device of claim 1 wherein each recess includes an entrance portion and an exit portion.

3. The counting device of claim 2 wherein the entrance portion includes a straight sided wall.

4. The counting device of claim 2 wherein the exit portion includes an angled wall.

5. The counting device of claim 4 wherein the entrance portion includes a straight sided wall, and wherein the locking unit and recesses are configured to permit one-way rotation of the shaft.

6. The counting device of claim 1 wherein the cover opening is a slot and wherein the position indicator extends, at least in part, into the slot.

7. The counting device of claim 1 including an end cap coupled to the locking plate by at least one fastener.

8. The counting device of claim 1 including a sterilization challenge specimen holder mounted thereto.

9. A counting device, comprising:
a threaded shaft;
a handle affixed to a first end of the threaded shaft, the handle including a locking unit on the handle spaced from the shaft;
a locking plate having an opening therein for receipt of the shaft, the locking plate spaced from the handle, the locking plate having a plurality of recesses in facing relation to the locking unit; and
a position indicating assembly unit coupled to the threaded shaft for movement as the handle is rotated, the position indicating assembly unit including a position indicator; and
indicia disposed for cooperation with the position indicator,
wherein the recesses are arranged in a circular pattern in the locking plate and cooperate with the locking unit such that the locking unit engages each of the recesses as the handle is rotated, wherein rotation of the handle moves the position indicator to indicate a count of handle movements, and wherein the position indicating assembly moves longitudinally along the shaft as the handle is rotated.

10. The counting device of claim 9 wherein the threaded shaft includes threads having a pitch and wherein the pitch is configured such that each rotation of the shaft moves the position indicating assembly a predetermined distance along the shaft.

11. A method of counting the uses of a device via a counting device, the method including the steps of:
rotating a handle affixed to a first end of a shaft, the shaft being at least partially threaded, the handle including a locking unit thereon spaced from the shaft; and
engaging the locking unit in a recess in a locking plate through which the shaft traverses, the locking unit arranged so as to cooperate with the recess,
wherein a position indicating assembly coupled to the shaft moves longitudinally along the shaft as the handle is rotated, and wherein longitudinal movement of the position indicating assembly indicates counts of uses of the device.

12. The method of claim 11 including a cover having a slot sized to accommodate a portion of the position indicating assembly.

13. The method of claim 12 wherein the slot is sized to accommodate a position indicator.

14. The method of claim 11 wherein each recess includes an entrance portion and an exit portion.

15. The method of claim 14 wherein the entrance portion includes a straight sided wall to prevent a rearward movement of the handle.

16. The method of claim 14 wherein the exit portion has a sloping wall.

17. The method of claim 11 wherein a pitch of the threads is set such that each rotation of the shaft moves the position indicating assembly a predetermined distance along the shaft.

* * * * *